United States Patent
Liang et al.

(10) Patent No.: US 7,296,894 B2
(45) Date of Patent: Nov. 20, 2007

(54) FUNDUS CAMERA HAVING SCANNED ILLUMINATION AND PUPIL TRACKING

(75) Inventors: Rongguang Liang, Penfield, NY (US); David Kessler, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 452 days.

(21) Appl. No.: 10/947,018

(22) Filed: Sep. 22, 2004

(65) Prior Publication Data
US 2006/0077347 A1    Apr. 13, 2006

(51) Int. Cl.
*A61B 3/14* (2006.01)

(52) U.S. Cl. .............. 351/206; 351/208; 351/209; 351/210; 351/220; 600/452; 396/18

(58) Field of Classification Search ........ 351/206–210, 351/220; 600/452; 606/4; 396/18, 51
See application file for complete search history.

(56) References Cited

U.S. PATENT DOCUMENTS

| | | | |
|---|---|---|---|
| 4,838,680 A | 6/1989 | Nunokawa | |
| 5,572,266 A | 11/1996 | Ohtsuka | |
| 5,713,047 A | 1/1998 | Kohayakawa | |
| 5,943,116 A | 8/1999 | Zeimer | |
| 6,546,198 B2 | 4/2003 | Ohtsuka | |
| 6,636,696 B2 | 10/2003 | Saito | |
| 7,001,019 B2 * | 2/2006 | Takagi et al. ............... 351/211 |
| 2001/0024178 A1 * | 9/2001 | Takeuchi et al. .............. 345/55 |
| 2002/0051118 A1 * | 5/2002 | Takagi et al. ............... 351/211 |

* cited by examiner

*Primary Examiner*—Hung X. Dang
*Assistant Examiner*—Joseph Martinez

(57) ABSTRACT

An apparatus (100) for obtaining an image of the eye, has an alignment section (160) for aligning the pupil of the eye along an optical axis and a pupil sensor (170) for identifying pupil location and dimensions. An illumination section (112) has a light source (114) for providing an illumination beam and a spatial light modulator (125) for positioning and shaping the illumination beam according to the sensed location and dimensions of the pupil. An illumination beam partitioning mechanism (50) segments the illumination beam directed toward the pupil of the eye into at least one light-bearing segment (150) and at least one blocked segment. An actuator (132) coupled to the illumination beam partitioning mechanism (50) scans the at least one light-bearing segment (150) of the illumination beam across the pupil of the eye. An image sensor (146), aligned along the optical axis, obtains reflected light from the eye.

46 Claims, 17 Drawing Sheets

FUNDUS CAMERA HAVING SCANNED ILLUMINATION AND PUPIL TRACKING

FIELD OF THE INVENTION

This invention generally relates to electronic imaging apparatus for fundus imaging and more particularly relates to an improved fundus imaging apparatus using scanned slit illumination and an electronically controlled aperture.

BACKGROUND OF THE INVENTION

Fundus camera imaging is acknowledged to be an important diagnostic tool for detection of various conditions affecting the eye, including diabetic retinopathy and macular degeneration. Various embodiments of fundus imaging apparatus are disclosed, for example in U.S. Pat. No. 5,713,047 (Kohayakawa); U.S. Pat. No. 5,943,116 (Zeimer); U.S. Pat. No. 5,572,266 (Ohtsuka); U.S. Pat. No. 4,838,680 (Nunokawa); U.S. Pat. No. 6,546,198 (Ohtsuka); and U.S. Pat. No. 6,636,696 (Saito).

While these patents attest to continuous improvements in fundus camera design, there are still significant hurdles to widespread acceptance and usability of these devices. Among disadvantages noted with current devices are high cost and complexity, difficulty of operation, large size, and image quality limitations. These disadvantages hinder the successful deployment of fundus cameras in primary care physician (PCP) offices or in medical test labs, where they could be used by a technician having relatively little training in device operation and imaging, to obtain images that can be assessed by specialists at some other location.

A further significant disadvantage of existing fundus imaging apparatus relates to the requirement for pupil dilation. For most patients, artificially induced enlargement of the pupil is necessary in order to allow sufficient light into the eye of the patient for fundus observation and image capture. At best, pupil dilation is uncomfortable and at least temporarily unsettling; at worst, dilation can even be dangerous for some individuals. A number of commercially available fundus imaging systems claim to be "non-mydriatic", that is, operable without pupil dilation. However, in practice, pupil dilation is still often required when using these apparatus.

The illumination optics subsystem of a conventional fundus imaging apparatus is designed in such a way that it requires pupil dilation for most patients. In order to provide a truly non-mydriatic fundus imaging system that renders pupil dilation unnecessary and that can be used by relatively untrained personnel, improved design of the illumination system would be required. However, the efforts of designers and manufacturers of these devices have been directed to providing more sophisticated imaging and assessment functions, many of which may actually require dilation in all cases. Thus, the limitations due to illumination subsystem design have been largely ignored and dilation is generally accepted as a requirement. For this reason, it can be seen that there is a need for an improved fundus imaging apparatus having an illumination system that allows fully non-mydriatic retinal imaging for a broad range of patients.

SUMMARY OF THE INVENTION

It is an object of the present invention to provide a fundus imaging apparatus having an improved illumination subsystem and imaging system that promotes non-mydriatic imaging. With this object in mind, the present invention provides an apparatus for obtaining an image of the eye, comprising:

a) an alignment section for aligning the pupil of the eye along an optical axis;

b) a pupil sensor for identifying location and dimensions of the pupil of the eye; and c) an illumination section for directing light through the pupil of the eye.

It is a feature of the present invention that it provides an illumination system for a fundus imaging apparatus that adapts the width of the illumination beam to the dimensions of the pupil, rather than requiring a fixed pupil width, as in conventional systems that require pupil dilation.

It is an advantage of the present invention that it minimizes or eliminates the requirement for pupil dilation for fundus imaging.

It is a further advantage of the present invention that it provides the capability for full-color fundus imaging.

It is yet a further advantage of the present invention that it provides a fundus imaging system with a larger field of view than conventional systems.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

DETAILED DESCRIPTION OF THE INVENTION

The present description is directed in particular to elements forming part of, or cooperating more directly with, apparatus in accordance with the invention. It is to be understood that elements not specifically shown or described may take various forms well known to those skilled in the art.

Conventional Illumination Arrangement

Figure 1:
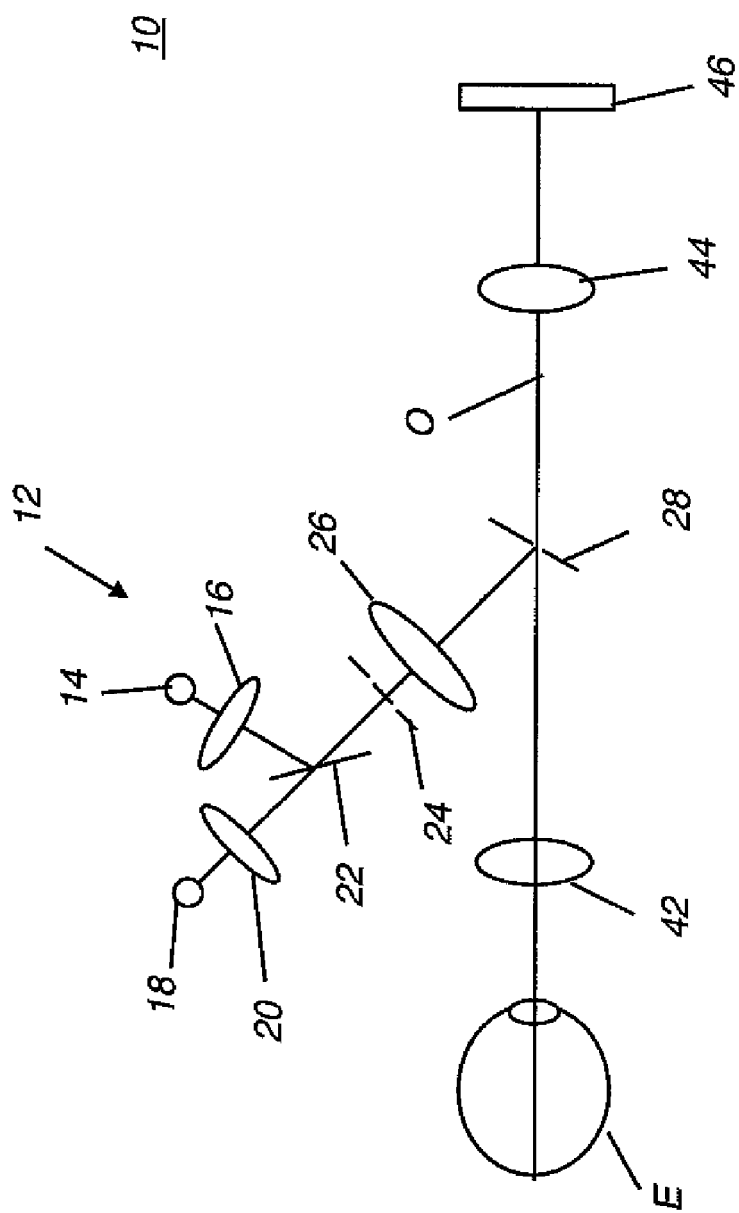
FIG. 1 is a schematic block diagram showing the overall arrangement of illumination apparatus components within a conventional fundus imaging apparatus.

In order to more fully appreciate the improved apparatus and method of the present invention, it is first instructive to review, at a high level, the operation of the illumination subsystem in a conventional fUndus imaging apparatus. Referring to FIG. 1, there is shown a hindus imaging apparatus 10 in which a conventional illumination section 12 is used. The patient's eye E is positioned along an optical axis O using an alignment subsystem, not shown in FIG. 1, but described subsequently. Illumination section 12 directs light either from an observation light source 14 and a lens 16 or from an image capture light source 18 and a lens 20 as controlled by control logic circuitry (not shown in FIG. 1). A half-minor 22 directs light from the appropriate source through a ring-slit diaphragm 24 and a lens 26, to an apertured minor 28. Apertured mirror 28 directs the illumination light along axis O and toward the pupil for illuminating the retina of eye E. Depending on the use of hindus imaging apparatus 10 at any one time, either observation light source 14 or image capture light source 18 is activated. Observation light source 14 is typically infrared (IR) light, to which eye E is insensitive. Image capture light source 18, on the other hand, may be a high-brightness source such as a xenon lamp, for example. Depending on the application, image capture light source 18 may be pulsed or strobed.

Figure 2:
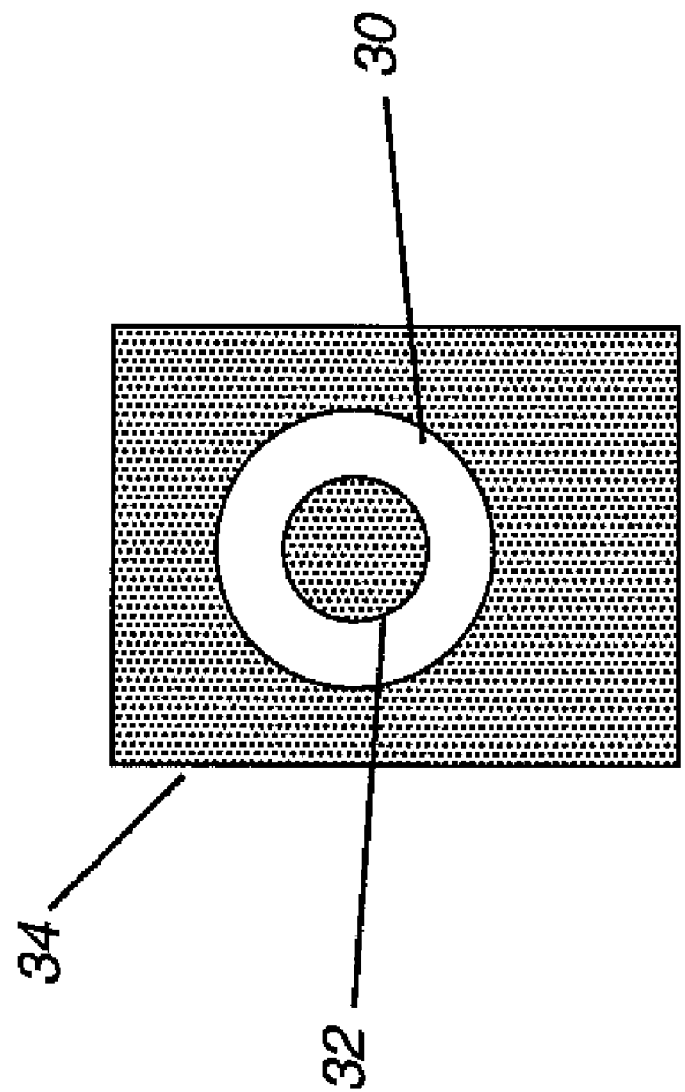
FIG. 2 is a plan view of a ring-slit diaphragm used in a conventional fundus imaging apparatus.

Ring-slit diaphragm 24 has the characteristic functional arrangement shown in FIG. 2. Light is transmitted through an inner ring 30 and is blocked at a middle section 32 and at an outer section 34. As is shown in the received illumination ring of FIG. 3, inner ring 30 is directed into a pupil 36 of the patient as a ring 40 of illumination. To obtain the retinal image, apertured mirror 28 (FIG. 1) has an aperture suitably centered about optical axis O to allow light that has been reflected from the retina of eye E and directed through lenses 42 and 44 to a sensor 46, such as a CCD.

The high-level block diagram of FIG. 1 thus gives an overview of illumination section 12 that applies for conventional fundus imaging apparatus. There have been numerous methods disclosed for optimizing the performance of illumination section 12, including components arranged to prevent stray reflected light from the cornea of eye E from being directed back toward sensor 46. However, the basic pattern of FIG. 1 is conventionally followed for these devices.

Figure 3:
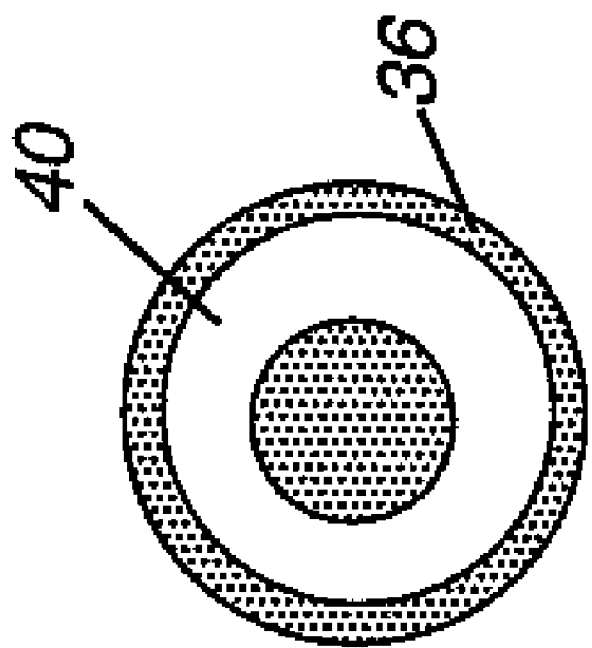
FIG. 3 is a plan view representation of the ring of illumination applied to the pupil of a patient in a conventional apparatus.

Among disadvantages of this conventional method is the relatively small field that is available. To compensate for this shortcoming, a series of tiled sections is typically imaged. In some cases, conventional image capture uses a narrow range of wavelengths, resulting in monochromatic images. The static ring 40 of illumination as shown in FIG. 3 is disadvantageous, since this ring occupies a portion of the image area during image capture. The combination of ring-slit diaphragm 24 and apertured mirror 28 acts to block scattered rays of illumination from the cornea, thereby obstructing these rays from affecting sensor 46. As yet another disadvantage, alignment of the patient's pupil with the conventional fundus imaging apparatus is time-consuming, since ring 40 must be fully inside the pupil and must avoid the iris.

Overview of Illumination Embodiments

The apparatus and method of the present invention eliminate the need for a separate ring of illumination, shown as static ring 40 in FIG. 3. Instead, the apparatus and method of the present invention use one or more moving members to selectively partition the illumination beam from either observation light source 14 or image capture light source 18, directing one or more partitions or segments of the illumination beam to eye E and allowing light reflected from the retina of eye E to be detected at sensor 46, while also blocking reflected light from the cornea of eye E from sensing components.

Figure 4:
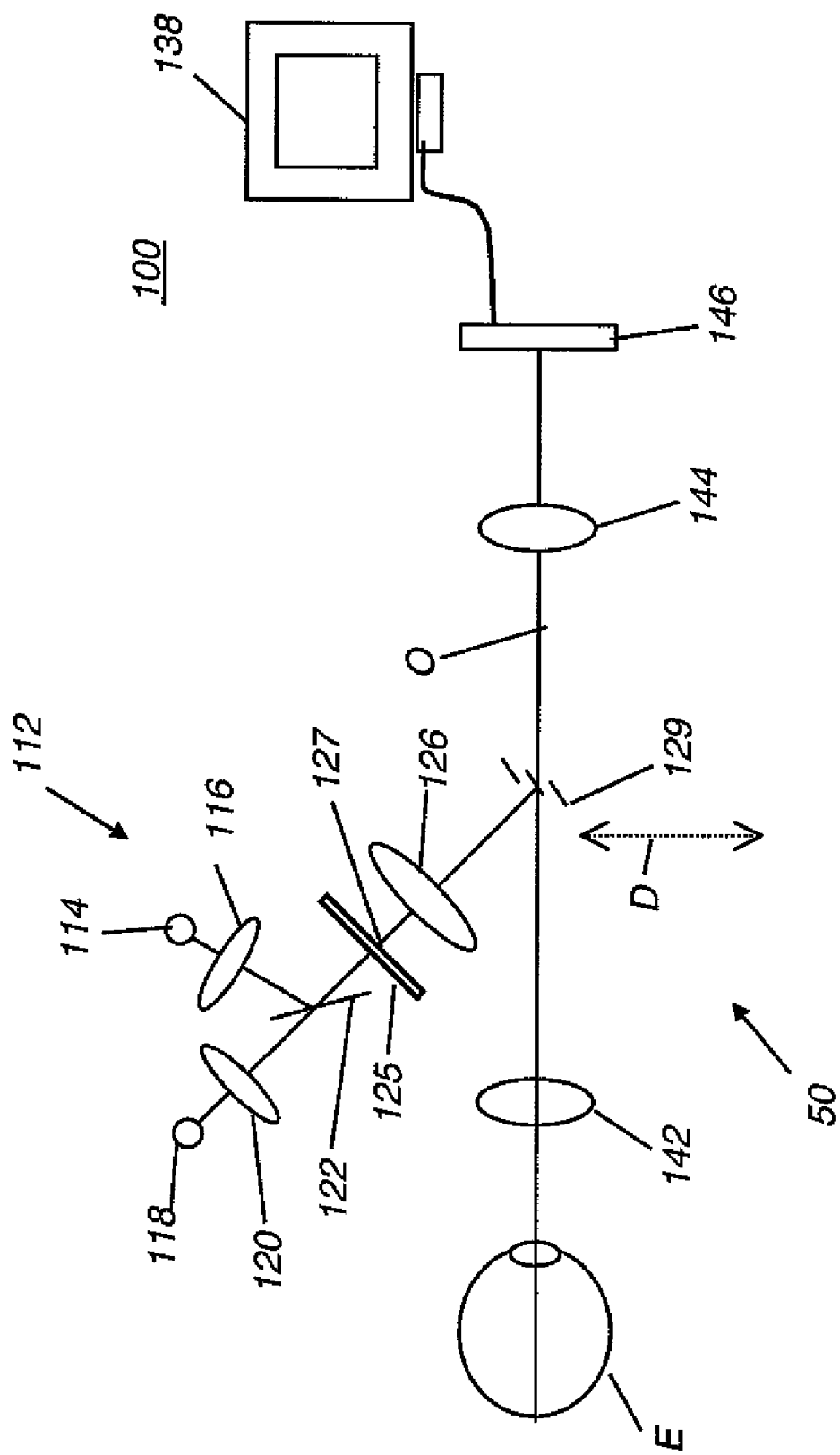
FIG. 4 is a schematic block diagram showing the overall arrangement of illumination apparatus components in a fundus imaging apparatus of the present invention.

Referring to FIG. 4, there is shown, in block diagram form, an overview of a fundus imaging apparatus 100 of the present invention. An illumination section 112 directs light either from an observation light source 114 and a lens 116 or from an image capture light source 118 and a lens 120 as controlled by control logic circuitry (not shown in FIG. 4). A half-mirror 122 or, alternately, a dichroic surface, directs light from the appropriate source through a transmissive spatial light modulator 125 which, acting as a type of transmissive light valve, provides an electronically controlled aperture 127 for the illumination beam, as described subsequently. The illumination beam is directed by a lens 126 to an illumination beam partitioning mechanism 50.

Illumination beam partitioning mechanism 50 segments the illumination beam cross-sectionally, as is described subsequently. To do this, illumination beam partitioning mechanism 50 uses a reciprocating partitioning member 129 in the embodiment of FIG. 4. Reciprocating partitioning member 129 moves in a direction D and scans one or more segments of the illumination beam through a lens 142 and into the eye E. Reflected light from the retina of eye E is then passed through reciprocating partitioning member 129, with unwanted reflected light from the cornea blocked. The light reflected from the retina is thus directed through a lens 144 to a sensor 146. A display 138, such as a CRT or LCD monitor, may be used in conjunction with sensor 146 and with cornea sensing camera or other sensing components, as described subsequently.

As the overview of FIG. 4 shows, illumination section 112 of the present invention directs the illumination beam from either observation light source 114 or image capture light source 118 toward the eye E and conditions the illumination beam in two ways:

(i) positioning and shaping the illumination beam through spatial light modulator 125; and
  (ii) partitioning the illumination beam at reciprocating partitioning member 129 into at least one illuminated segment that receives its corresponding partition of the illumination beam and at least one blocked segment that has its corresponding portion of the illumination beam blocked and, further, scanning the at least one illuminated segment along the field, thereby illuminating the complete field over time.

This dimensioning and conditioning of the illumination beam and method of scanning provide exceptional advantages for effecting a truly non-mydriatic illumination system for retinal imaging. It is worthwhile to observe that, while steps (i) and (ii) above are executed in this order in the embodiments described herein, a different order could be used, so that the illumination beam is first partitioned (step ii, above), then shaped (step i, above).

Shaping the Illumination Beam

The conventional ring-slit illumination method described with reference to FIGS. 1-3 directs a static ring 40 of illumination to the eye E being imaged. Among the problems inherent to this approach is its relatively poor adaptability to the dimensions of the pupil of eye E. Not only can pupils have different diameters from one patient to the next, but the actual shape of the pupil itself can vary from circular shape. Dilated pupils for different patients, for example, can vary in diameter between about 6 and 8 mm. Conventional fundus imaging systems reach some compromise for variable pupil dimensions using methods such as a variety of selectable ring-slit diaphragms 24. For example, a set of different ring-slit diaphragms 24, or other apertured devices, can be provided on a selector wheel or other mechanism, allowing an operator to select the aperture that is best suited to the dimensions of the patient's pupils. Any aperture selected in the place of ring-slit diaphragm 24 is, at best, an approximation and must fit the illumination ring 40 within the outer dimensions of the pupil for best operation. Providing illumination that extends even slightly beyond the borders of the pupil of eye E is not optimal, since stray, diffused light from the surrounding iris of eye E can easily be directed back along optical axis O and degrade image quality obtained at sensor 46.

Figure 5:
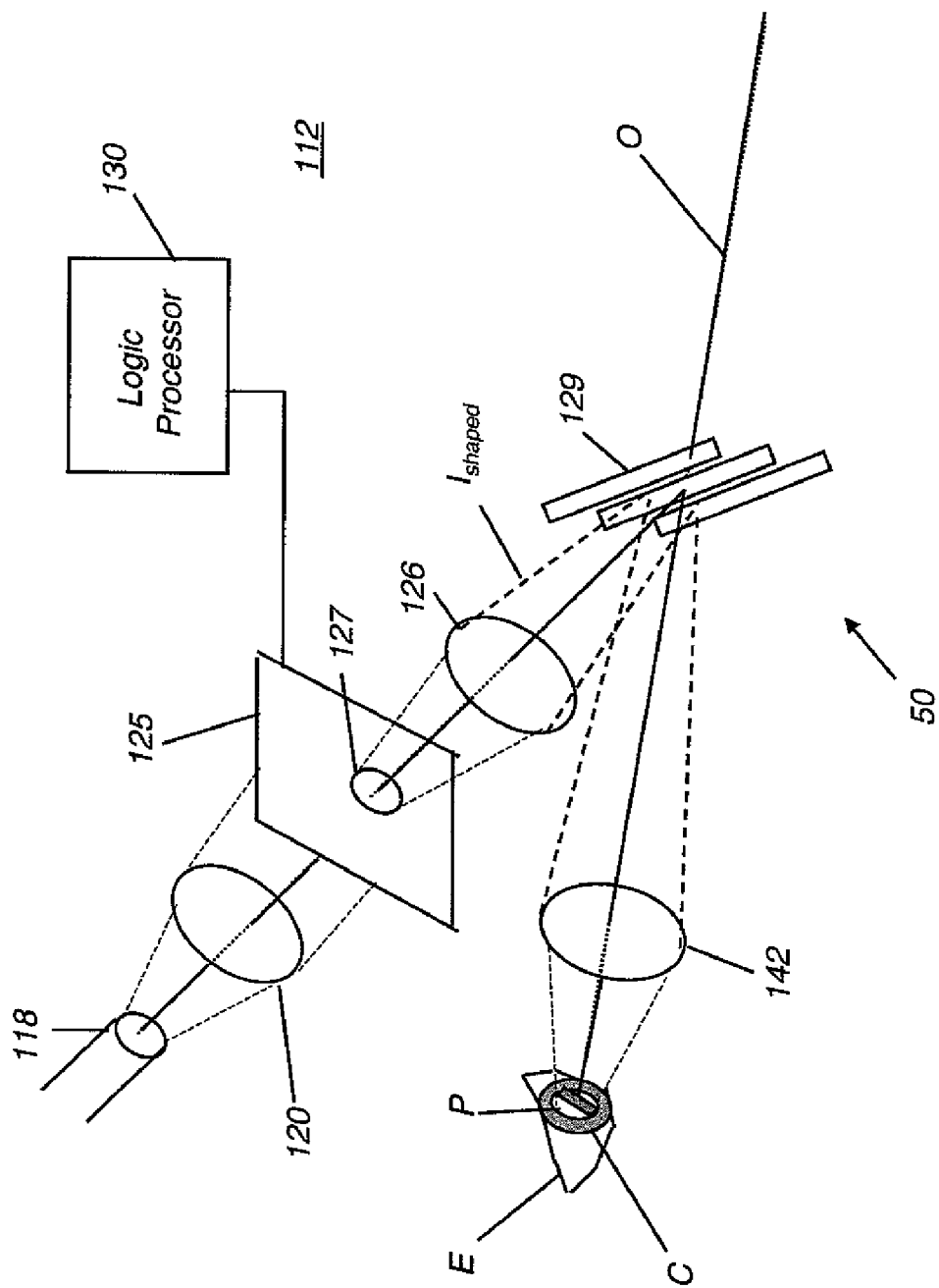
FIG. 5 is a perspective block diagram showing the beam shaping behavior of the illumination apparatus of the present invention.
Figure 6A:
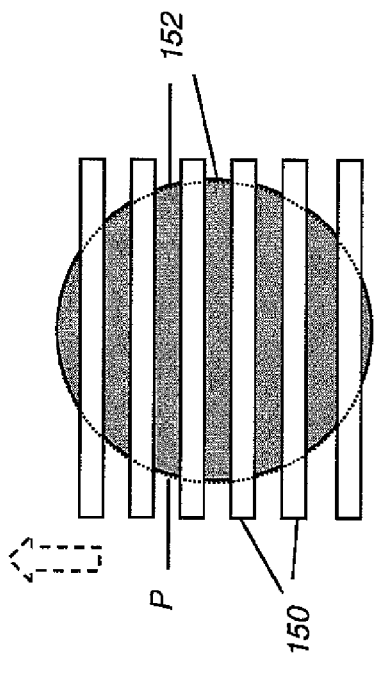
FIGS. 6A-6D are plan views showing the partition scanning used for illuminating the pupil using the apparatus and method of the present invention.
Figure 6B:
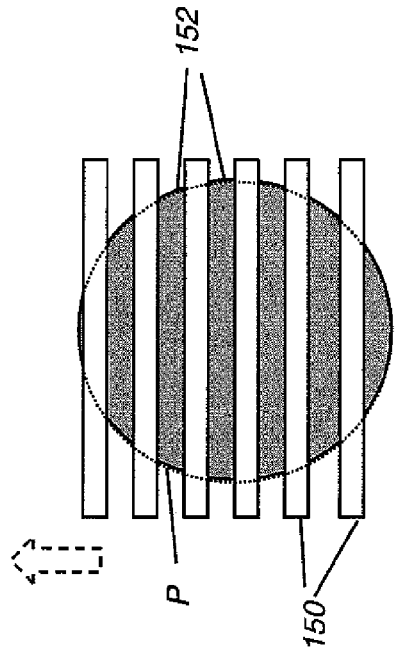
Figure 6C:
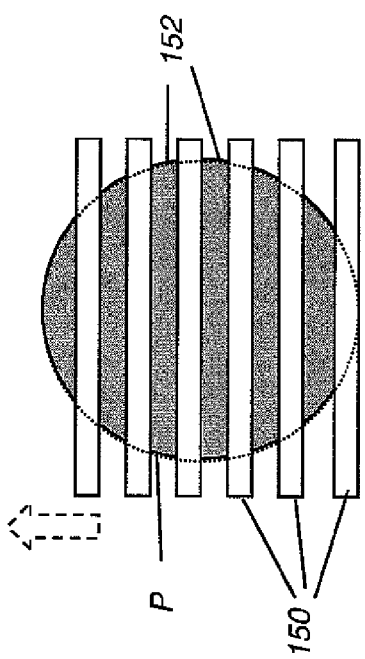
Figure 6D:
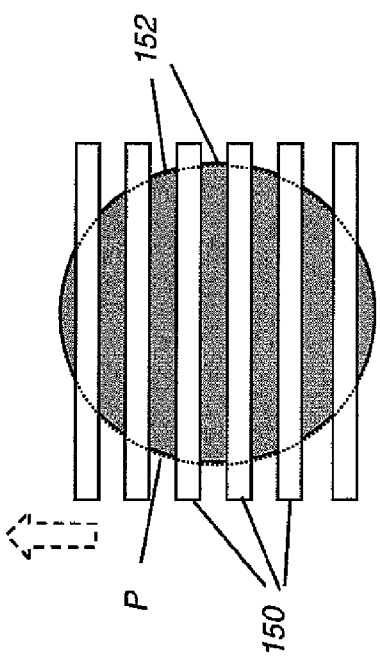

The apparatus and method of the present invention approaches this problem in a different manner, by shaping the illumination beam according to the detected coordinates of the pupil. This method shapes the illumination beam, when considered in cross-sectional profile, to match dimensional profile of the pupil, in size, placement, and overall shape. Referring to FIG. 5, there is shown, in perspective view, the optical path of illumination to the pupil from image capture light source 118. It must be noted that the same beam shaping operation applies for light from either image capture light source 118 or observation light source 114. In FIG. 5, light from image capture light source 118 is directed through lens 120 toward spatial light modulator 125, which provides an electronically controlled aperture 127 that is sized to correspond to the outline of pupil P of eye E. Electronically controlled aperture 127 provides a mask for the illumination beam to form a shaped illumination beam $I_{shaped}$, which is directed through lens 126 and goes to illumination beam partitioning mechanism 50. Here, shaped illumination beam $I_{shaped}$, is segmented and reflected from reciprocating partitioning member 129 or other component, then through lens 142 to pupil P.

There are a number of ways to provide electronically controlled aperture 127 for conditioning the cross-sectional profile of the illumination beam. Spatial light modulator 125 may be a transmissive LCD, for example, such as an LCD spatial light modulator, blocking light from around electronically controlled aperture 127 in a masking pattern that corresponds to pupil P coordinates and dimensions. In this way, illumination can be directed to the full area of pupil P, but not extending outside the circumference of pupil P.

In one embodiment, the outline of pupil P is detected by an electronic camera or other sensor, as described subsequently. Image data from this camera is processed by a control logic processor 130, as shown in FIG. 5, to determine pupil P position and dimensional coordinates using pattern recognition and other imaging algorithms such as outline detection algorithms, employing methods familiar to those skilled in the imaging arts. Overall, the mechanism used as pupil sensor may have any of a number of components and may be fully automated or require operator interaction, such as for centering of sensor measurements or for verification of pupil outline and dimensions. This pupil sensing subsystem may also include feedback and adjustment mechanisms for adapting to subtle changes in pupil position over time.

Figure 17:
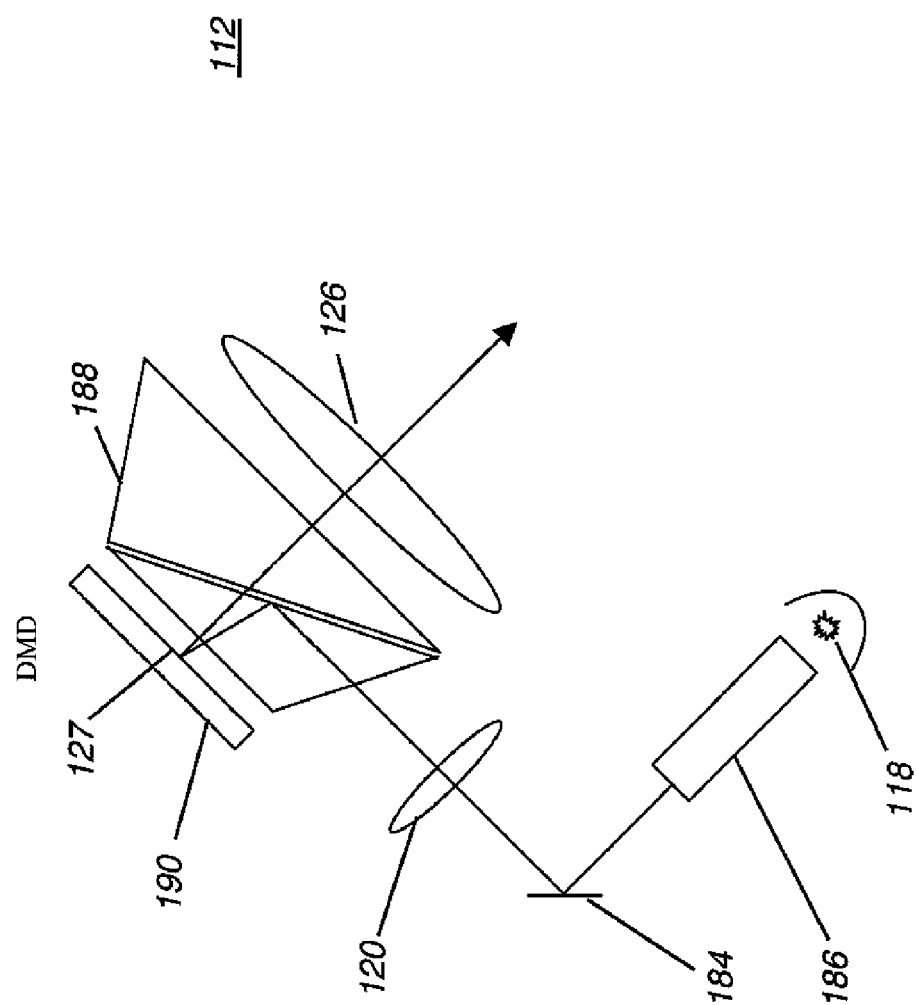
FIG. 17 is a block diagram showing an alternate embodiment for illumination components.

It must be noted that mechanisms other than transmissive spatial light modulators 125 could be used to provide electronically controlled aperture 127 for beam shaping. Reflective spatial light modulators and light valves could also be used for this purpose, as is shown in FIG. 17. Here, image capture light source 118 provides light that may be conditioned by a uniformizer 186 or other component and directed, by an optional mirror 184, through lens 120 and to a prism 188 or a beamsplitter of some type. Prism 188 directs the light toward a reflective light valve, such as a digital micromirror device 190 in the embodiment of FIG. 17. Digital micromirror device 190 then provides electronically controlled aperture 127, modulating the incident light to provide, through lens 126, an illumination beam that is shaped, in cross-sectional profile, according to data provided about the dimensions and position of the pupil. A similar arrangement to that of FIG. 17 would be used for a reflective LCD spatial light modulator used in place of digital micromirror device 190, with a polarization beamsplitter providing the light directing function of prism 188.

Partitioning the Illumination Beam

For obtaining an image, the full shaped illumination beam $I_{shaped}$ provided through spatial light modulator 125 in FIG. 5 cannot be provided to pupil P. If this were to happen, there would be excessive light reflection from the cornea C of eye E, resulting in unacceptably poor image quality. Instead, the present invention provides a cross-sectional partitioning or segmenting of the illumination beam. Referring to the sequence shown in FIGS. 6A-6D, the circular shape represents the two-dimensional shape of the patient's pupil P, to which the two-dimensional cross-section of the illumination beam, as shaped by illumination section 112, corresponds. As described with reference to FIGS. 4 and 5, the shape of P describes the cross-sectional "envelope" of the illumination beam, as modulated through spatial light modulator 125 or other device that provides electronically controlled aperture 127. Reciprocating partitioning member 129 of FIGS. 4 and 5, acting as illumination beam partitioning mechanism 50, segments the illumination beam to provide one or more light-bearing partitions 150 separated by one or more non-light-bearing partitions 152. Movement of reciprocating partitioning member 129 then scans the segmented illumination provided by light-bearing partitions across the area of pupil P. In the sequence of FIGS. 6A-6D, scanning is effected in the direction of the outlined arrow. Following this overall pattern, reciprocating partitioning member 129 partitions shaped illumination beam $I_{shaped}$ so that, at any instant, one or more light-bearing partitions 150 or segments of the shaped illumination beam $I_{shaped}$ are directed into pupil P. These light-bearing partitions 150 are then shifted in position to provide a scanning effect over the pupil that enables the complete image to be obtained over time.

Figure 7:
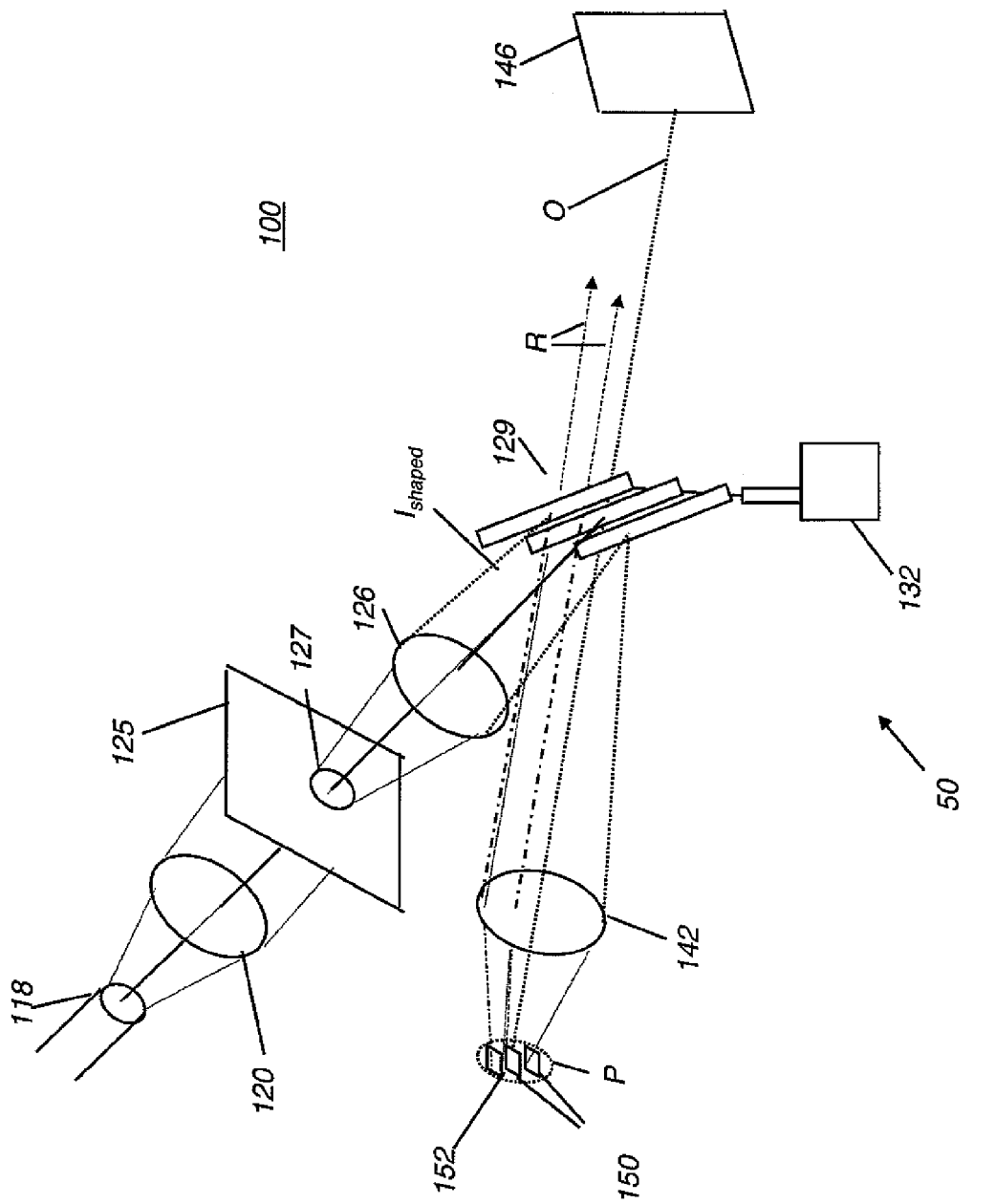
FIG. 7 is a perspective block diagram showing the beam partitioning behavior of the illumination apparatus of the present invention.

Referring to FIG. 7, the result of this partitioning behavior of reciprocating partitioning member 129 within fundus imaging apparatus 100 is shown for one embodiment. Reciprocating partitioning member 129 reflects shaped illumination beam $I_{shaped}$ from spatial light modulator 125 along optical axis O towards the pupil P (shown in dotted outline in FIG. 7), with this light segmented into a set of light-bearing partitions 150 separated by non-light-bearing partitions 152. Reflected light R from the eye then travels back along optical axis O. The unwanted reflected light from the cornea is substantially blocked by suitable portions of reciprocating partitioning member 129. The desired light from the retina is transmitted to sensor 146. To provide scanning action that allows a complete image to be obtained over time, an actuator 132 is coupled to reciprocating partitioning member 129 to provide reciprocating movement.

Figure 8:
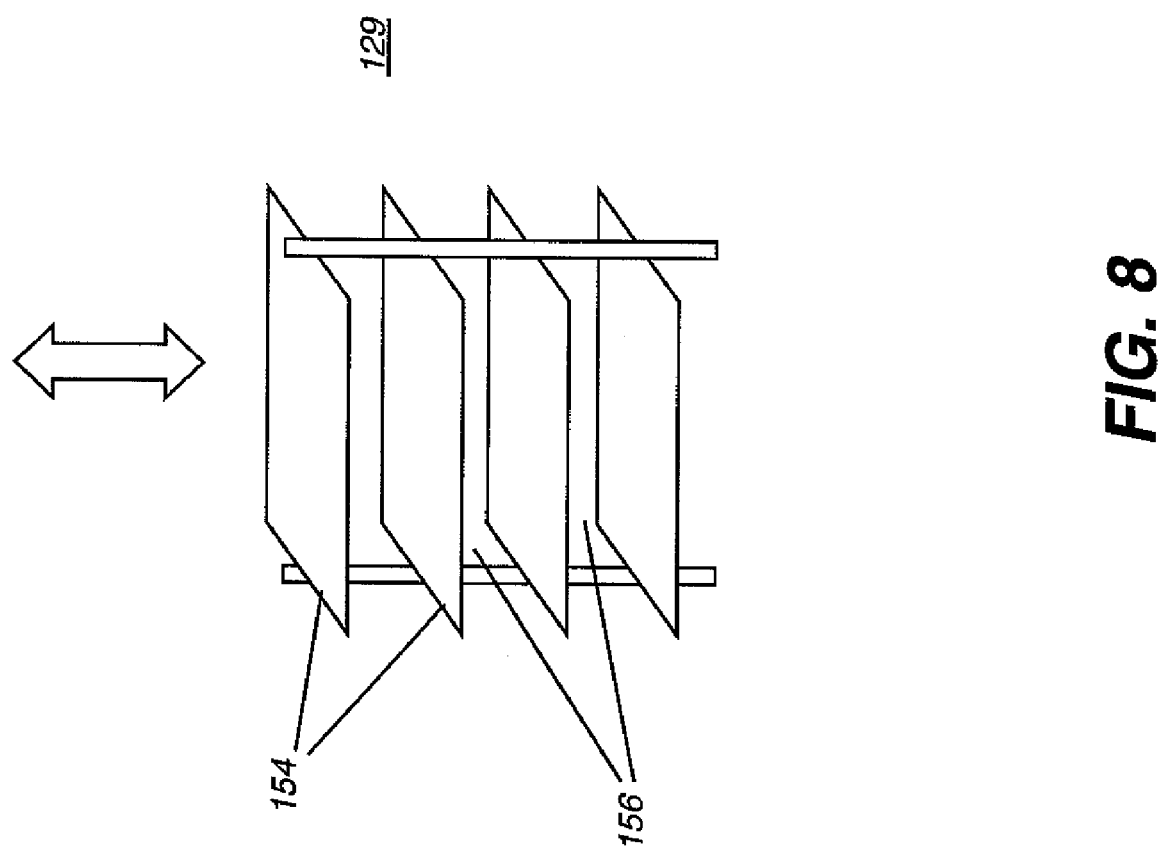
FIG. 8 is a perspective view showing a reciprocating partitioning member in one embodiment of the present invention.

One embodiment of reciprocating partitioning member 129 is shown in FIG. 8. One or more reflective members 154 reflects light into light-bearing partitions 150. Gaps 156 between reflective members 154 correspond to non light-bearing partitions 152 of FIGS. 6A-6D, enabling the return of reflected light from the eye along the optical axis O to sensor 146. As the double arrow in FIG. 8 indicates, reciprocating partitioning member 129 is moved up or down during scanning operation, in order to bathe the complete pupil P of eye E in light over time, using scanned light-bearing partitions 150 to reflect the shaped illumination beam $I_{shaped}$ appropriately. The arrangement of reflective members 154 can have any number of alternate embodiments for partitioning the shaped illumination beam $I_{shaped}$. Reciprocating actuation, represented by actuator 132 in FIG. 7, can be provided by any number of electromechanical devices, including a solenoid, motor, piezoelectric actuator, pneumatic device, spring-loaded actuator, or other device. The speed of movement provided for this scanning effect can be varied, based on the response characteristics of sensor 146, the brightness of shaped illumination beam $I_{shaped}$, and other factors.

Figure 9:
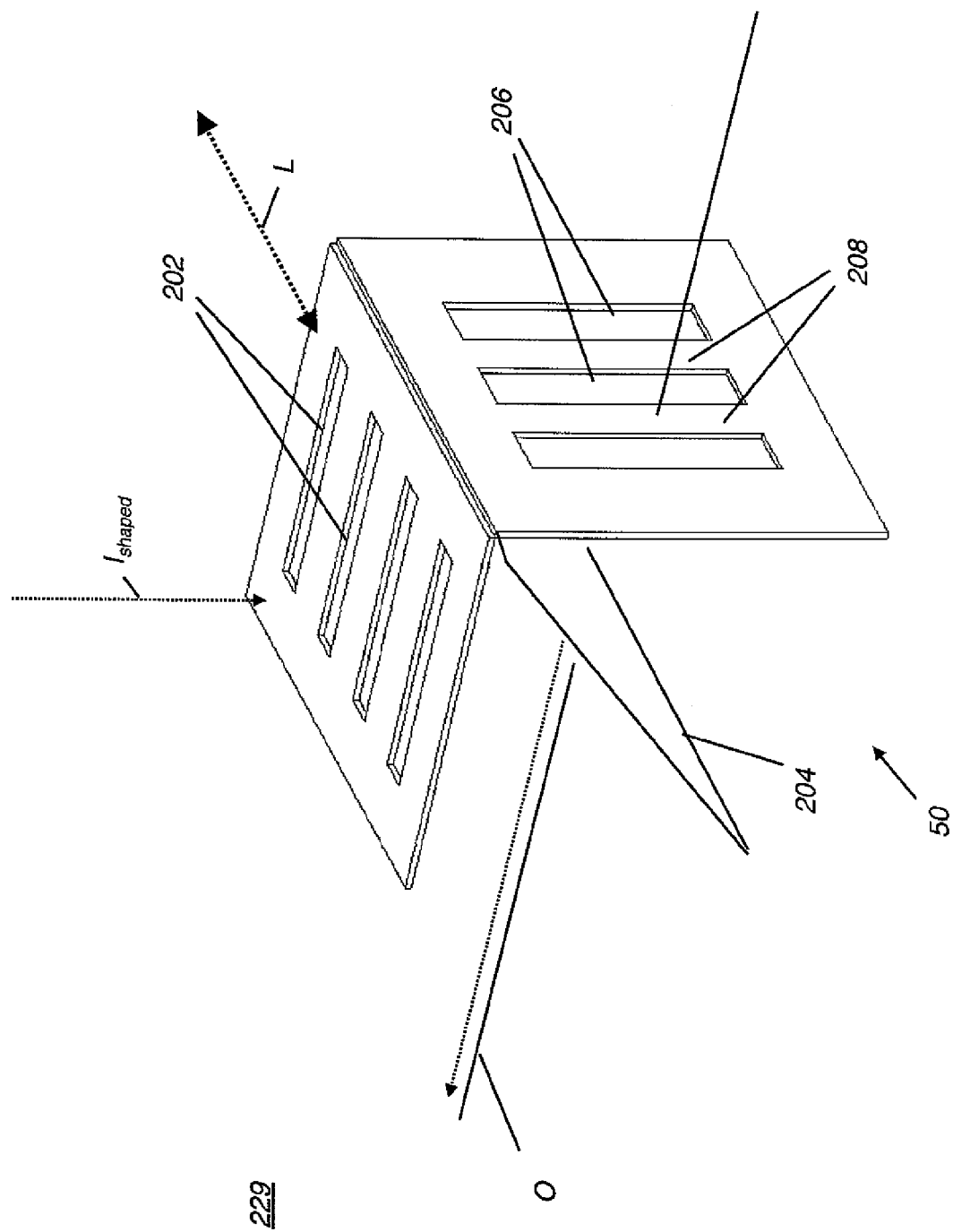
FIG. 9 is a perspective view showing an alternate reciprocating partitioning member in one embodiment of the present invention.

An alternate embodiment for partitioning the pupil as illumination beam partitioning mechanism 50 is shown in FIG. 9. Here, a reciprocating partitioning member 229, disposed within the path of shaped illumination beam $I_{shaped}$, has one or more slits 202 that provide an aperture for illumination. A beamsplitter 204 directs the partitioned illumination along optical axis O and toward the eye of the patient, following the general pattern of FIG. 4. Light reflected from the eye, returning along optical axis O, is directed toward sensor 146 though apertures 206. One or more blocking members 208 block light reflected back from the corneal surface, so that the reflected light that goes to sensor 146 is from the retina. For scanning the complete pupil, linear movement is provided in the direction of arrow L in FIG. 9.

As the examples of FIGS. 8 and 9 clearly show, there can be a number of ways for implementing the overall function of illumination beam partitioning mechanism 50 performed by reciprocating partitioning member 129, 229 of the present invention. This component partitions the shaped illumination beam $I_{shaped}$ into distinct light-bearing and non-light-bearing partitions 150 and 152, scans light-bearing and non-light-bearing partitions 150 and 152 across the pupil to illuminate the full field over time, and blocks unwanted light that is reflected from the cornea.

Fundus Imaging Apparatus

Figure 10:
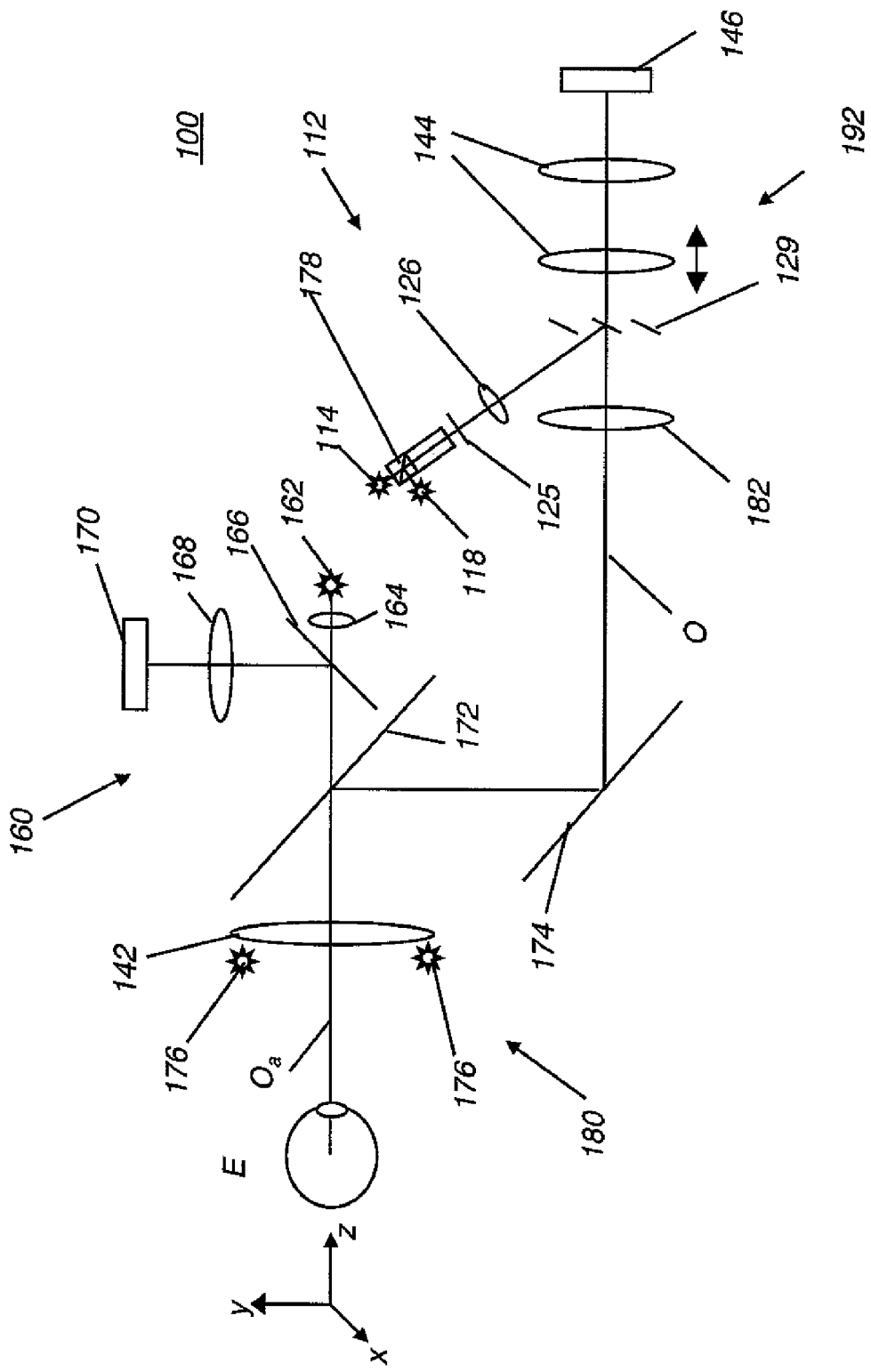
FIG. 10 is a block diagram of a fundus imaging apparatus in one embodiment.
Figure 11:
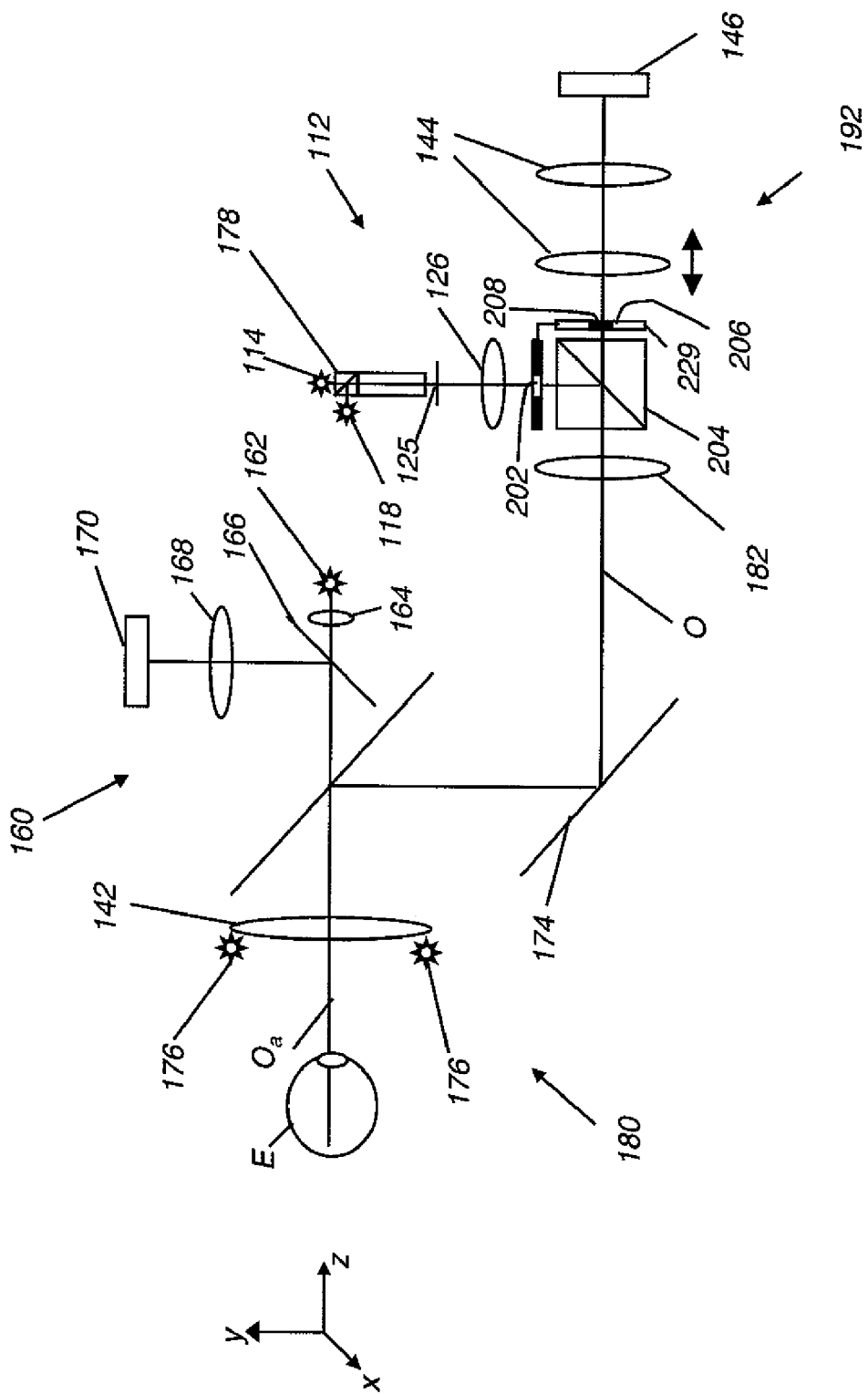
FIG. 11 is a block diagram of a fundus imaging apparatus in another embodiment.

Referring to FIG. 10, there is shown a block diagram of fundus imaging apparatus 100 in one embodiment of the present invention. In addition to illumination section 112 described above, fundus imaging apparatus 100 has an alignment section 160, a cornea focusing section 180, and a retina focusing section 192. FIG. 11 shows an alternate embodiment of a fundus imaging apparatus 200 using reciprocating partitioning member 229.

Figure 12:
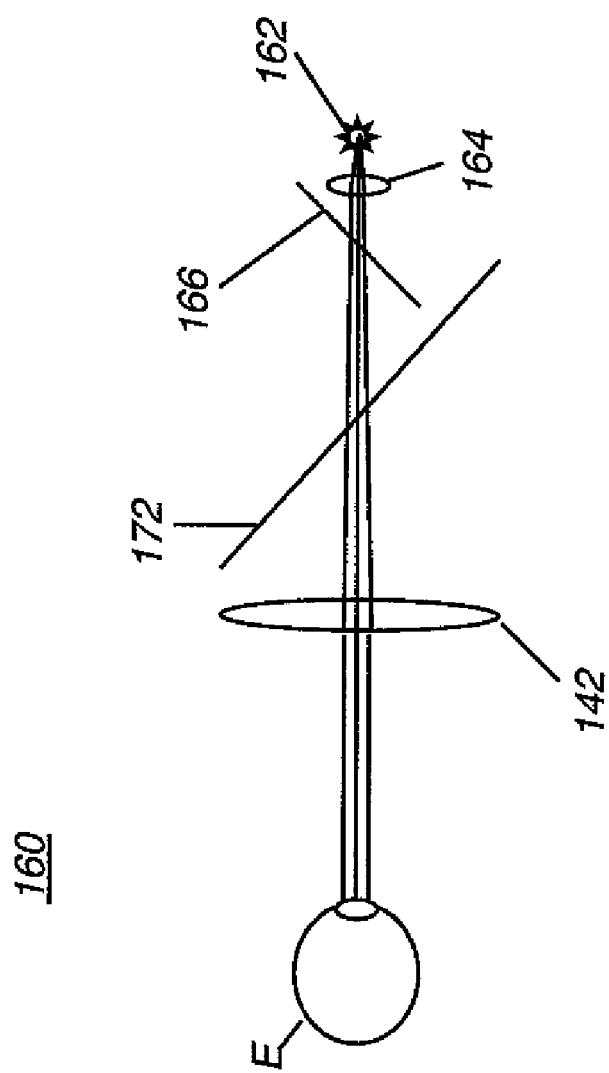
FIG. 12 is a block diagram of the alignment section of a fundus imaging apparatus.

Alignment section 160 provides aiming and accommodation of the patient's vision, in order to position the eye E favorably for fundus imaging. To simplify description, FIG. 12 isolates the basic components of alignment section 160 from the block diagrams of FIGS. 10 and 11. An aiming target 162, such as an LED or other light source, visible through beamsplitters 172 and 166, is used to direct the eye of the patient to a position that provides visual accommodation. That is, when viewing aiming target 162 through lens 142 and a lens assembly 164, the light entering eye E is substantially collimated. When the light entering eye E is collimated, light from illumination section 112 can be directed to the retina and more accurate focus adjustments can be made. Relative to the coordinate axes shown in FIG. 10, the alignment procedure along optical axis $O_a$ sets the position of eye E along the z axis, and provides alignment positioning relative to the orthogonal x and y axes.

FIGS. 10 and 11 also show different embodiments of illumination section 112 in more detail. A beamsplitter 178 in illumination section 112 directs light from either observation light source 114 or image capture light source 118 through spatial light modulator 125 and lens 126 for beam shaping and to reciprocating partitioning member 129 (FIG. 10) or 229 (FIG. 11) as illumination beam partitioning mechanism 50 for partitioning illumination to the pupil as was described generally with reference to FIGS. 6A-6D. Lenses 182 and 142 direct the shaped and partitioned illumination beam into the pupil of eye E. Beamsplitters 172 and 174 fold optical axis O between lenses 182 and 142.

Figure 13:
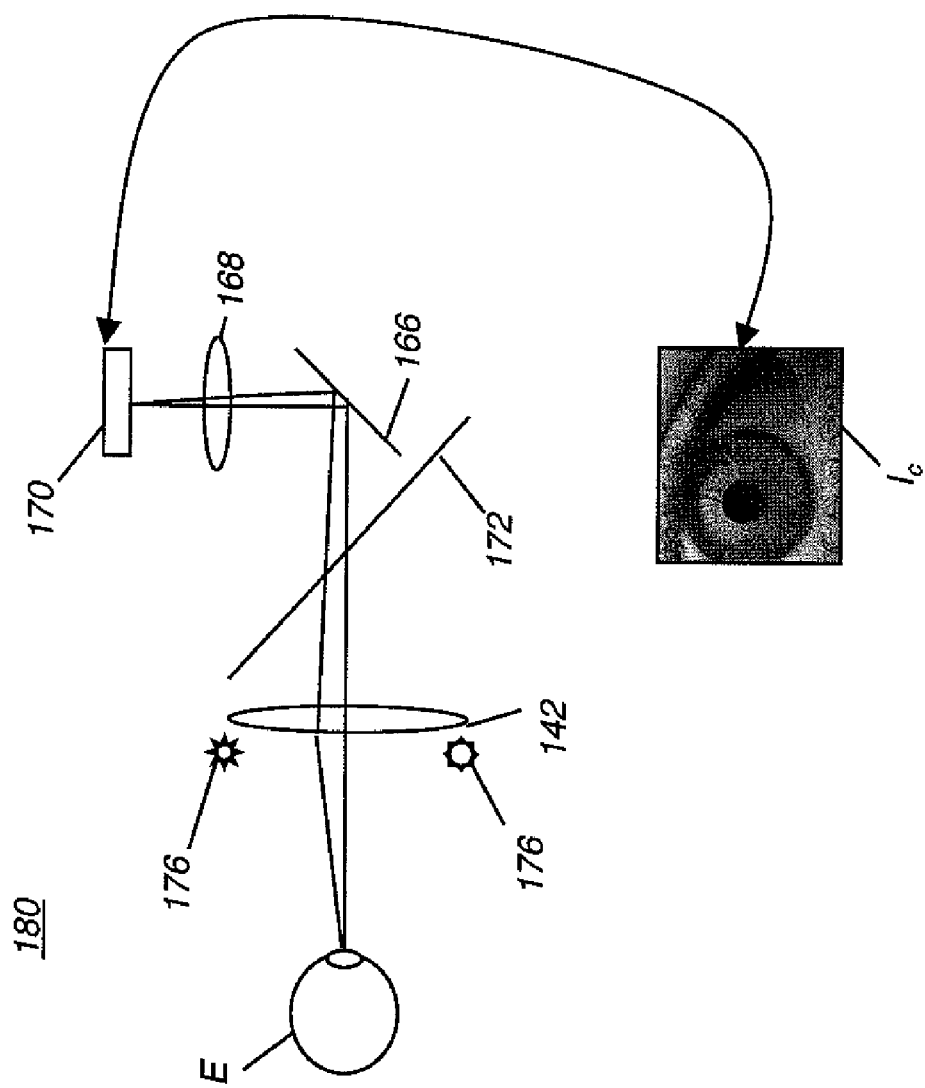
FIG. 13 is a block diagram of the cornea focusing section of a fundus imaging apparatus.

Once alignment of eye E is achieved, it is necessary to focus on the cornea using cornea focusing section 180. To simplify description, FIG. 13 isolates the basic components of cornea focusing section 180 from the block diagrams of FIGS. 10 and 11. With respect to FIG. 13, the purpose of cornea focusing section 180 is to adjust the focus of lens 142 or, with reference to FIGS. 10 and 11, to adjust for the position of the eye along the z-axis. When necessary to focus the cornea, light sources 176 provide peripheral illumination to the cornea. The reflected light is then directed, through beamsplitters 172 and 166 and through lens 168, to cornea camera 170, which is optically conjugate to the cornea. Cornea camera 170 can be a relatively inexpensive imaging device, requiring only that it have sufficient resolution for focusing. In one embodiment, for example, cornea camera 170 is a CCD camera, model no. IK-52V manufactured by Toshiba.

Figure 14:
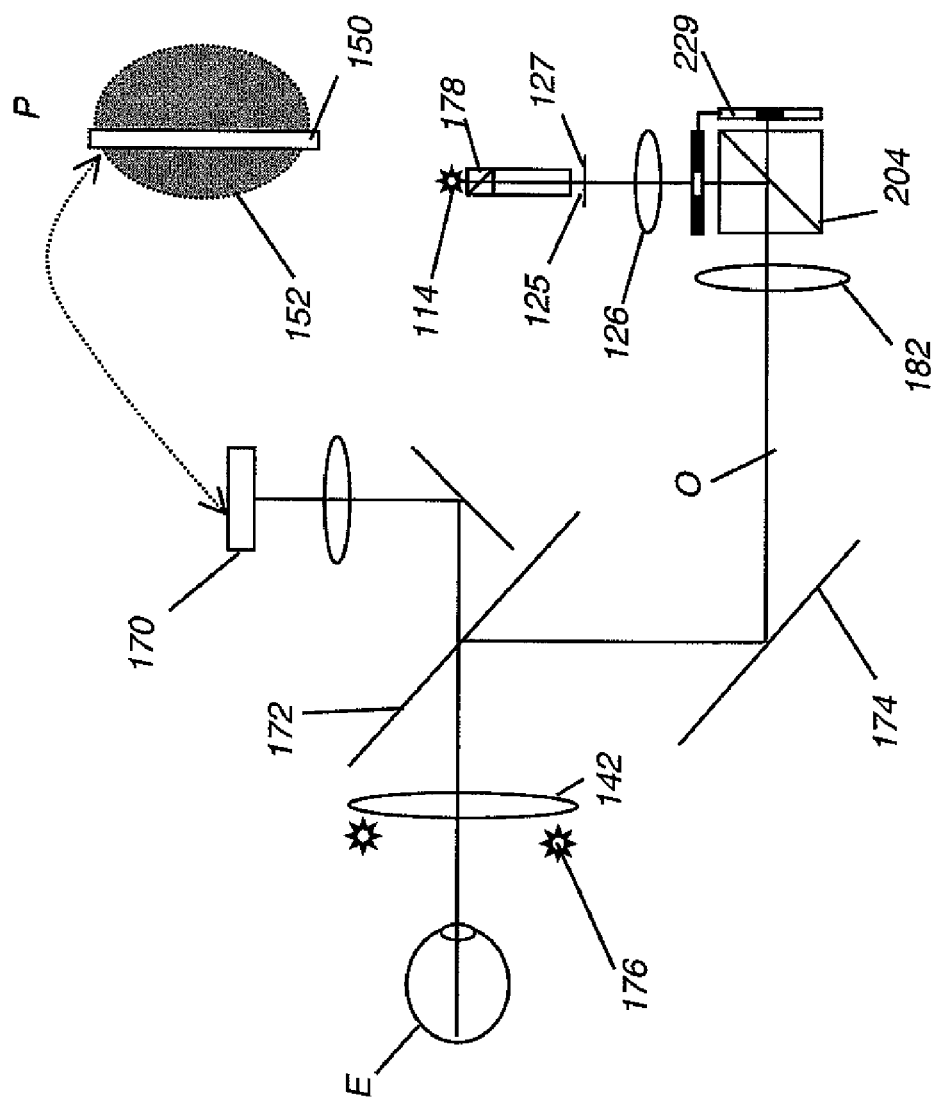
FIG. 14 is a block diagram of components used in preliminary retinal focusing.

Achieving proper focus of the cornea allows the retinal image to be obtained. As a first step, partitioned, shaped illumination beam $I_{shaped}$ is directed onto the cornea, imaging reciprocating partitioning member 129 or 229 onto the cornea. To simplify description for this step, FIG. 14 isolates the basic components used for this phase of retinal focus setup from the block diagrams of FIGS. 10 and 11. Observation light source 114 is conjugate with the cornea. For observation functions, an IR LED or similar source for observation light source 114 is directed through transmissive spatial light modulator 125 for beam shaping and through reciprocating partitioning member 229 and beamsplitter 204 for partitioning, then directed to the cornea of eye E along optical axis O. Cornea camera 170 detects the image of reciprocating partitioning member 229, which can be displayed on an accompanying CRT monitor (not shown) for example.

It must be observed that light sources 176, used for initial stages of cornea focus, are disabled during the step of cornea focus described with respect to FIG. 14. It must also be noted that similar behavior occurs whether reciprocating partitioning member 129 of FIG. 8 or reciprocating partitioning member 229 of FIG. 9 is used. Light-bearing partitions 150 and non-light-bearing partitions 152, once properly focused in this manner, can be scanned over the area of a pupil P to provide full retinal illumination.

Once the partitioned, shaped illumination beam $I_{shaped}$ is directed onto the cornea for observation, thereby forming an image of reciprocating partitioning member 129 or 229 onto the cornea, final adjustments can be made for sizing electronically controlled aperture 127 provided by transmissive spatial light modulator 125. In addition, any necessary final adjustments to retinal focus can be made. To simplify description for this step, FIG. 15 isolates the basic components used for final retinal focus from the block diagrams of FIGS. 10 and 11.

Figure 15:
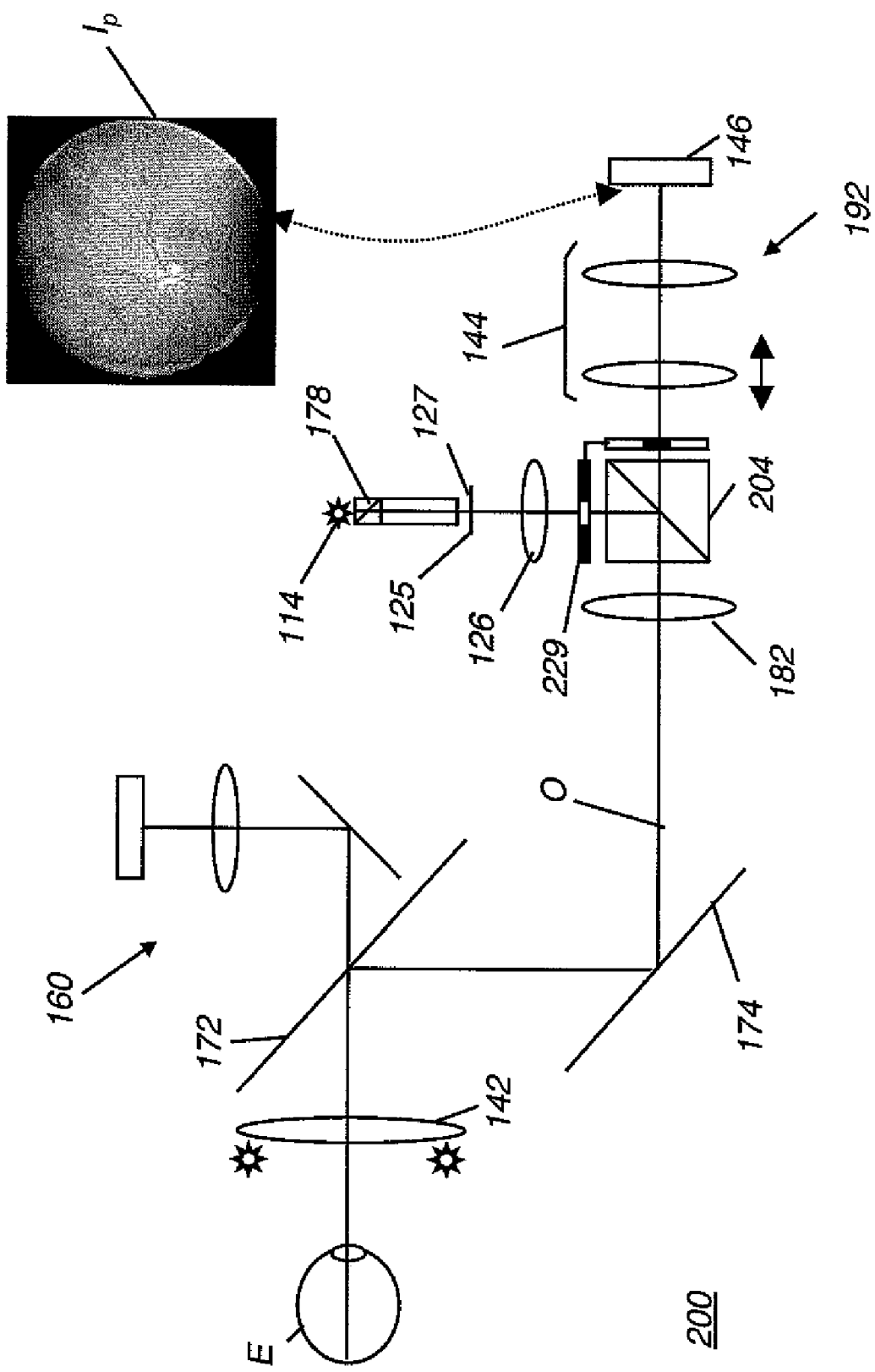
FIG. 15 is a block diagram of components used for preview and retinal focus.

Referring to FIG. 15, observation light source 114 provides illumination that is shaped and partitioned by illumination section 112, using either reciprocating partitioning member 129 or 229, for example. Lenses 182 and 142 cooperate to focus the partitioned, shaped illumination beam $I_{shaped}$ onto the cornea. The path of light reflected from the retina goes back through reciprocating partitioning member 129 or 229, which blocks at least a substantial portion of light reflected from the cornea. The retinal image is thereby made available, in scanned partition format, to sensor 146. A preview image $I_p$ is then displayed to the operator to enable focus adjustment of lens 144.

Figure 16:
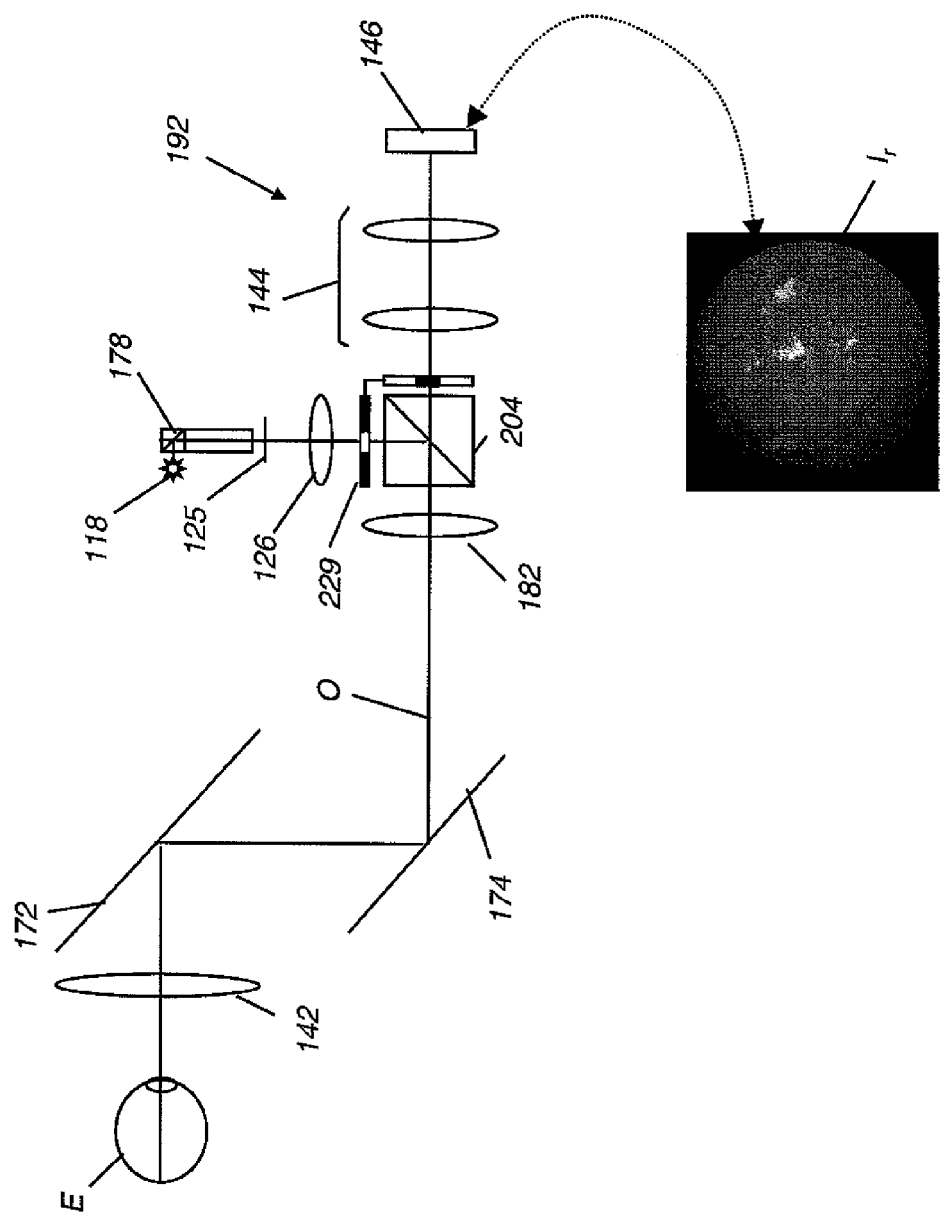
FIG. 16 is a block diagram of the imaging component path according to the present invention.

With the retina focused using preview image $I_p$, the retinal image can now be obtained. To simplify description for this step, FIG. 16 isolates the basic components used for retinal imaging from the block diagrams of FIGS. 10 and 11. Image capture light source 118, typically a visible light source, is now energized, producing a beam of illumination that is shaped and partitioned by illumination section 112, using either reciprocating partitioning member 129 or 229, for example. Lenses 182 and 142 cooperate to focus the partitioned, shaped illumination beam $I_{shaped}$ onto the cornea. As with the preview illumination described with reference to FIG. 15, the path of light reflected from the retina goes back through reciprocating partitioning member 129 or 229, which blocks at least a substantial portion of light reflected from the cornea. The retinal image is thereby made available, in scanned partition format, to sensor 146. A retina image $I_r$ is then displayed to the operator and can be stored electronically for transfer to some other location or for additional processing.

During image capture, it may be useful to continually recheck eye E alignment as well as cornea and retinal focus. This type of continuous checking could be executed automatically or could be incorporated into operator procedures. For example, light sources 176 could be periodically energized to provide the operator with the opportunity for making any necessary focus readjustments.

The present invention provides a fundus imaging apparatus that is simple to operate, allows compact packaging, and does not require dilation of the pupil for most patients. It must be emphasized that fundus imaging apparatus 100 or 200, as described in the present application, is primarily intended to provide basic fundus imaging that can be inexpensively performed at the office of a PCP or other non-specialist site. Thus, more advanced imaging features and functions are omitted from this description of fundus imaging apparatus 100 and 200. However, the same apparatus and methods used for illumination of the eye described hereinabove could also be applied to a more sophisticated imaging device. In particular, methods for scanning the retina with illumination may prove beneficial for other types of ophthalmic imaging devices.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, the various light sources used within fundus imaging apparatus 100 or 200 allow a number of optional types. Sensors and CCD devices could be any of a number of different types. Although the resolution and overall image quality requirements for cornea camera 170 and sensor 146 are quite different, a single CCD array could be used for both cornea camera 170 and sensor 146, switched between these functions, using techniques well known in the imaging arts.

Within illumination beam partitioning mechanism 50, various types of actuators and mechanisms could be used for performing the functions of scanning reciprocating partitioning member 129, 229. Possible actuator types include electromagnetic and piezoelectric actuators or acoustical transducers. Alternately, devices used could be spring-mounted. Other types of electromechanical actuators could be used.

Thus, what is provided is an apparatus and method for fundus imaging using scanned illumination.

PARTS LIST

10 fundus imaging apparatus
12 illumination section
14 observation light source
16 lens
18 image capture light source
20 lens
22 half-mirror
24 ring-slit diaphragm
26 lens
28 apertured mirror
30 inner ring
32 middle section
34 outer section
36 pupil
40 ring
42 lens
44 lens
46 sensor
50 illumination beam partitioning mechanism
100 fundus imaging apparatus
112 illumination section
114 observation light source
116 lens
118 image capture light source
120 lens
122 half-mirror
125 spatial light modulator
126 lens
127 electronically controlled aperture 129 reciprocating partitioning member
130 control logic processor
132 actuator
138 display
142 lens
144 lens
146 sensor
150 light-bearing partition
152 non-light-bearing partition
154 reflective member
156 gap
160 alignment section
162 aiming target
164 lens assembly
166 beamsplitter
168 lens
170 cornea camera
172 beamsplitter
174 beamsplitter
176 light source
178 beamsplitter
180 cornea focusing section
182 lens
184 mirror
186 uniformizer
188 prism
190 digital micromirror device
192 retina focusing section
200 fundus imaging apparatus
202 slit
204 beamsplitter
206 aperture
208 blocking member
229 reciprocating partitioning member

The invention claimed is:

1. An apparatus for obtaining an image of an eye, comprising:
   (a) an alignment section for aligning a pupil of the eye along an optical axis;
   (b) a pupil sensor for identifying location and dimensions of the pupil of the eye;
   (c) an illumination section for directing light through the pupil of the eye, comprising:
      (i) a light source for providing an illumination beam;
      (ii) a spatial light modulator for positioning and shaping the illumination beam according to the sensed location and dimensions of the pupil;
      (iii) an illumination beam partitioning mechanism for segmenting the illumination beam directed toward the pupil of the eye into at least one light-bearing segment and at least one blocked segment;
      (iv) an actuator coupled to the illumination beam partitioning mechanism for scanning the at least one light-bearing segment of the illumination beam across the pupil of the eye; and
   (d) an image sensor, aligned along the optical axis, for obtaining reflected light from the eye.

2. An apparatus according to claim 1 wherein the light source is taken from the group consisting of an IR laser, an LED, and a lamp.

3. An apparatus according to claim 1 wherein the spatial light modulator is a transmissive liquid crystal device.

4. An apparatus according to claim 1 wherein the spatial light modulator is a digital micromirror device.

5. An apparatus according to claim 1 wherein the illumination beam partitioning mechanism comprises a plurality of reflectors.

6. An apparatus according to claim 1 wherein the actuator is taken from the group consisting of a piezoeleetric actuator, a motor, an acoustic actuator, an electromagnetic actuator, a pneumatic actuator, and a spring-loaded actuator.

7. An apparatus according to claim 1 wherein the pupil sensor comprises an image detection algorithm.

8. An apparatus according to claim 1 wherein the optical axis extends along a longitudinal axis of the eye.

9. An apparatus according to claim 1 wherein the spatial light modulator is positioned between the light source and the illumination beam partitioning mechanism.

10. An apparatus according to claim 1 wherein the illumination section further includes a lens disposed between the spatial light modulator and the illumination beam partitioning mechanism.

11. An apparatus according to claim 1 wherein the spatial light modulator further includes an electronically controlled aperture.

12. An apparatus according to claim 1 wherein the spatial light modulator regulates passage of the illumination beam from the light source to the illumination beam partitioning mechanism.

13. An apparatus according to claim 1 wherein a portion of the image sensor is substantially normal to the optical axis.

14. The apparatus according to claim 1 further including a first lens and a second lens, the first and second lenses being aligned along the optical axis, the first lens being disposed between the illumination beam partitioning mechanism and the image sensor.

15. The apparatus according to claim 14 further including a third lens disposed between the light source and the illumination beam partitioning mechanism.

16. The apparatus according to claim 15 further including a half mirror disposed between the third lens and the illumination beam partitioning mechanism.

17. An apparatus for illuminating an eye, comprising:
   (a) a light source for providing an illumination beam;
   (b) a spatial light modulator for positioning and cross-sectionally shaping the illumination beam according to a location and dimensions of a pupil;
   (c) an illumination beam partitioning mechanism for cross-sectionally segmenting the illumination beam directed toward the pupil of the eye into at least one light-bearing segment and at least one blocked segment; and
   (d) a scanner for scanning the at least one light-bearing segment of the illumination beam across the pupil of the eye.

18. An apparatus according to claim 17 further comprising a pupil sensor for identifying location and dimensions of the pupil of the eye.

19. An apparatus according to claim 17 wherein the scanner comprises an actuator taken from the group consisting of a piezoelectric actuator, a motor, an acoustic actuator, an electromagnetic actuator, a pneumatic actuator, and a spring-loaded actuator.

20. An apparatus according to claim 18 wherein the pupil sensor comprises an image detection algorithm.

21. An apparatus according to claim 17 wherein the light source is taken from the group consisting of an IR laser, an LED, and a lamp.

22. An apparatus according to claim 17 wherein the spatial light modulator is a transmissive liquid crystal device.

23. An apparatus according to claim 17 wherein the spatial light modulator is a digital micromirror device.

24. An apparatus according to claim 17 wherein the illumination beam partitioning mechanism comprises a plurality of reflectors.

25. The apparatus according to claim 17, further including an image sensor aligned along an optical axis of the eye.

26. An apparatus according to claim 25 wherein a portion of the image sensor is substantially normal to the optical axis.

27. An apparatus according to claim 17 wherein the optical axis extends along a longitudinal axis of the eye.

28. The apparatus according to claim 25 further including a first lens and a second lens, the first and second lenses being aligned along the optical axis, the first lens being disposed between the illumination beam partitioning mechanism and the image sensor.

29. The apparatus according to claim 28 further including a third lens disposed between the light source and the illumination beam partitioning mechanism.

30. The apparatus according to claim 29 further including a half mirror disposed between the third lens and the illumination beam partitioning mechanism.

31. An apparatus according to claim 17 wherein the spatial light modulator is positioned between the light source and the illumination beam partitioning mechanism.

32. An apparatus according to claim 17 wherein the illumination section further includes a lens disposed between the spatial light modulator and the illumination beam partitioning mechanism.

33. An apparatus according to claim 17 wherein the spatial light modulator further includes an electronically controlled aperture.

34. An apparatus according to claim 17 wherein the spatial light modulator regulates passage of the illumination beam from the light source to the illumination beam partitioning mechanism.

35. A method for illuminating a human eye for obtaining an image comprising:
   (a) aligning the eye along an optical axis;
   (b) obtaining a dimensional profile of a pupil of the eye;
   (c) generating an illumination beam;
   (d) shaping a cross-sectional profile of the illumination beam according to the dimensional profile obtained of the pupil of the eye; and
   (e) directing the shaped illumination beam toward the eye, along the optical axis.

36. A method according to claim 35 further comprising:
   (f) partitioning the illumination beam to block light from at least one partition of the beam, thereby forming at least one blocked segment of the beam not bearing light and at least one light-bearing segment of the beam; and
   (g) scanning the light-bearing segment of the illumination beam along the pupil of the eye to illuminate successive portions of the eye over time.

37. A method according to claim 35 wherein the step of obtaining a dimensional profile of the pupil of the eye comprises the step of executing an image sensing algorithm.

38. A method according to claim 35 wherein the step of shaping the cross-sectional profile of the illumination beam comprises the step of directing the illumination beam toward a transmissive spatial light modulator.

39. A method according to claim 35 wherein the step of scanning the light-bearing segment of the illumination beam comprises the step of actuating an actuator.

40. The method according to claim 35 wherein the step of obtaining a dimensional profile includes the step of processing image data in a feedback control loop.

41. The method according to claim 35 wherein the step of aligning the eye includes directing the eye to an aiming target.

42. The method according to claim 35 further including generating a peripheral illumination beam and directing the peripheral illumination beam to a cornea of the eye.

43. The method according to claim 35 further including generating a peripheral illumination beam and directing the peripheral illumination beam to a cornea of the eye.

44. A method for illuminating a human eye for obtaining an image comprising:
   (a) aligning the eye along an optical axis;
   (b) obtaining dimensional information about a pupil of the eye;
   (c) generating an illumination beam;
   (d) shaping the cross-sectional profile of the illumination beam according to the dimensional information obtained about the pupil of the eye;
   (e) partitioning the illumination beam to block light from at least one partition of the beam, thereby forming at least one blocked segment of the beam not bearing light and at least one light-bearing segment of the beam; and
   (f) scanning the light-bearing segment of the illumination beam along the pupil of the eye to illuminate successive portions of the eye over time.

45. The method according to claim 44 wherein the step of obtaining dimensional information includes the step of processing image data in a feedback control loop.

46. The method according to claim 44 wherein the step of aligning the eye includes directing the eye to an aiming target.

* * * * *